(12) United States Patent
Baumann et al.

(10) Patent No.: US 9,433,876 B2
(45) Date of Patent: Sep. 6, 2016

(54) CLAMPING DEVICE FOR CLAMPING A PLURALITY OF COLUMNS FOR SAMPLE PREPARATION

(71) Applicant: LCTech GmbH, Dorfen (DE)

(72) Inventors: Maximilian Baumann, Munich (DE); Martin Brandlhuber, St. Wolfgang (DE); Uwe Aulwurm, Velden/Vils (DE)

(73) Assignee: LCTech GmbH (DE)

( * ) Notice: Subject to any disclaimer, the term of this patent is extended or adjusted under 35 U.S.C. 154(b) by 61 days.

(21) Appl. No.: 14/182,036

(22) Filed: Feb. 17, 2014

(65) Prior Publication Data

US 2014/0231330 A1 Aug. 21, 2014

(30) Foreign Application Priority Data

Feb. 18, 2013 (DE) .................. 10 2013 101 596

(51) Int. Cl.
| | |
|---|---|
| *B01D 15/22* | (2006.01) |
| *G01N 30/46* | (2006.01) |
| *G01N 30/60* | (2006.01) |
| *B01D 15/10* | (2006.01) |
| *B01D 15/18* | (2006.01) |

(52) U.S. Cl.
CPC ............. *B01D 15/22* (2013.01); *G01N 30/461* (2013.01); *G01N 30/465* (2013.01); *B01D 15/1864* (2013.01); *B01D 15/1871* (2013.01); *B01D 15/1878* (2013.01); *G01N 30/6004* (2013.01); *G01N 30/6039* (2013.01); *G01N 30/6047* (2013.01); *G01N 30/6065* (2013.01)

(58) Field of Classification Search
CPC .. G01N 30/02; G01N 30/60; G01N 30/6034; G01N 30/6004; G01N 30/6039; G01N 30/6047; G01N 30/46; G01N 30/461; G01N 30/465; B01D 15/10; B01D 15/22; B01D 15/18; B01D 15/1864; B01D 15/1871; B01D 15/1878
See application file for complete search history.

(56) References Cited

U.S. PATENT DOCUMENTS

| | | | |
|---|---|---|---|
| 3,615,235 A | 10/1971 | Hrdina et al. | |
| 4,451,365 A | 5/1984 | Sattler et al. | |
| 4,732,672 A | 3/1988 | Kiang et al. | |
| 5,601,707 A * | 2/1997 | Clay et al. ................. | 210/198.2 |
| 8,307,541 B2 | 11/2012 | Ford et al. | |
| 2005/0011821 A1 | 1/2005 | Held et al. | |
| 2005/0211617 A1* | 9/2005 | Held et al. ................. | 210/198.2 |
| 2006/0243651 A1 | 11/2006 | Ricker | |
| 2010/0154207 A1* | 6/2010 | Ford et al. ...................... | 29/700 |

* cited by examiner

*Primary Examiner* — Katherine Zalasky
(74) *Attorney, Agent, or Firm* — Renner Kenner Greive Bobak Taylor & Weber (57) ABSTRACT

A clamping device for clamping a plurality of columns for sample preparation provides a plurality of clamping blocks and a displacement mechanism for displacing at least one clamping block relative to an opposing clamping block between an open position and a clamping position. At least three clamping blocks are retained in a row one behind the other on a guiding rail so that at least two columns can be clamped in an axial direction one behind the other between the clamping blocks. First and second slidingly displaceable clamping blocks of the least three clamping blocks are retained on the guiding rail and connected to the displacement mechanism by coupling means so that an actuation of the displacement mechanism from the clamping position into the open position brings about a displacement of all the slidingly displaceable clamping blocks and the columns are released.

13 Claims, 6 Drawing Sheets

CLAMPING DEVICE FOR CLAMPING A PLURALITY OF COLUMNS FOR SAMPLE PREPARATION

The invention relates to a clamping device for clamping a plurality of columns for sample preparation, in particular for analysing chemical materials, such as, for example, for chromatography.

DE 31 43 075 A1 discloses, for example, a device for clamping and rapidly changing columns for fluid chromatography. In this instance, one or more columns are clamped parallel beside each other between clamping blocks which contain supply and discharge lines for a solvent. U.S. Pat. No. 4,732,672 A also discloses a device for rapidly clamping and changing a column between two displaceable clamping blocks. Furthermore, it is known from US 2006/0243651 A1 to arrange columns for such arrangements in an axial direction one behind the other.

DE 1 801 684 A relates to a flow-through reactor which enables the retention of two columns which are arranged one above the other and which are fixed by means of a lower, a central and an upper retention member. In order to change the columns, the retention members can be displaced along a common retention rod after securing screws are released.

An object of the invention is to provide a space-saving, flexible and easy-to-operate clamping device for clamping a plurality of columns for sample preparation.

According to the invention, this object is achieved by a clamping device for clamping a plurality of columns for sample preparation which provides for a plurality of clamping blocks and a displacement mechanism for displacing at least one clamping block relative to an opposing clamping block between an open position and a clamping position. In this instance, in the open position, a column can be inserted between two opposing clamping blocks and, in the clamping position, the inserted column is clamped between the opposing clamping blocks in order to produce a fluid connection between the column and at least one of the opposing clamping blocks. In this instance, at least three clamping blocks are retained in a row one behind the other on a guiding rail so that at least two columns can be clamped in an axial direction one behind the other between the clamping blocks. The slidingly displaceable clamping blocks which are retained on the guiding rail are connected to the displacement mechanism by coupling means in such a manner that an actuation of the displacement mechanism from the clamping position into the open position brings about a displacement of all the slidingly displaceable clamping blocks and the columns are released.

Owing to the arrangement of the clamping blocks on the guiding rail, the clamping device can be adapted to different column lengths in a very rapid and uncomplicated manner. Another advantage of the axial arrangement is also that the fluid connection between the columns, if desired, is comparatively short.

According to a preferred embodiment of the invention, one of the clamping blocks is arranged in a fixed manner on the guiding rail whilst at least two other clamping blocks are retained on the guiding rail in a slidingly displaceable manner. In this instance, the clamping block which is arranged in a fixed manner on the guiding rail can form one end of the row of clamping blocks which are arranged one behind the other, whilst at least the last, slidingly displaceable clamping block at the other end of the row is operationally connected to the displacement mechanism in order to displace the last slidingly displaceable clamping block relative to the fixed clamping block. A displacement of the slidingly displaceable clamping block which is connected to the displacement mechanism in the direction of the fixed clamping block in this instance also brings about a displacement of all the clamping blocks which are arranged therebetween together with the inserted columns as far as the clamping position. With the displacement of a clamping block, therefore, a large number of columns can be clamped in a fluid-tight manner.

In particular with relatively long columns, it may be advantageous to provide between two clamping blocks at least one column retention member for orientated retention of the column in the open position.

Furthermore, each clamping block may have at least one connection piece, which cooperates with a closure element of the column in the clamping position in order to produce the fluid connection between the column and the clamping block. In this instance, the fluid connection between the connection piece and closure element may, for example, be produced by means of a cone and counter-cone, the cone being provided either on the connection piece or on the closure element and the counter-cone being provided on the correspondingly other portion. Such an embodiment has the advantage that the columns become self-centred during clamping.

A particularly advantageous arrangement is produced when the central clamping blocks which are arranged between the first and last clamping block each have two connection pieces which are arranged at opposing sides of the respective clamping block. These central clamping blocks can consequently each be coupled to two columns.

Each clamping block may further have at least one fluid channel which opens at one end in the connection piece and at the other end thereof at a connection location. In this instance, it is also conceivable for the connection location to be formed by another connection piece at an opposing side of the clamping block. In this manner, a comparatively short connection could be produced between two adjacent columns. For many applications, however, it will be advantageous for the connection locations of the fluid channels to be provided at one of the sides of the clamping block. At this location, the fluid channels can then be connected to an external valve arrangement in order to produce the flow paths which are advantageous for the respective application through the individual columns.

The displacement mechanism is advantageously constructed for displacement of the at least one clamping block in both directions along the guiding rail. It may comprise an electrically, hydraulically or pneumatically operated actuator. Furthermore, the displacement mechanism may have at least one force-limiting compensation spring, a displacement force which is produced by means of the displacement mechanism being transmitted via the compensation spring to the at least one slidingly displaceable clamping block. Owing to this compensation spring, the displacement force which is transmitted via the columns is limited and thereby prevents an overload of the columns. In the case of the use of a hydraulic or pneumatic actuator, the compensation spring may be dispensed with.

According to the invention, the slidingly displaceable clamping blocks which are retained on the guiding rail are connected to the displacement mechanism by way of coupling means in such a manner that an actuation of the displacement mechanism from the clamping position into the open position brings about a displacement of all the slidingly displaceable clamping blocks. The columns are thereby released and a simple removal of the columns is enabled. These coupling means may, for example, be formed by a rod, with carrier elements, or a Bowden cable. The coupling means are constructed in such a manner that they carry the clamping blocks only in the direction from the clamping position into the open position.

According to a second embodiment of the invention, however, it would also be conceivable for the coupling means to carry the clamping blocks in both displacement directions. In this embodiment, it would be advantageous for at least one force-limiting compensation spring to be provided between each slidingly displaceable clamping block and the coupling means in order to limit the clamping force between the column and the clamping blocks. Such an embodiment reduces the forces transmitted via the columns so that columns of a softer material, or having a smaller pressure tolerance could also be used.

Other embodiments and advantages of the invention are explained in greater detail with reference to the following description and the drawings, in which.

Figure 1:
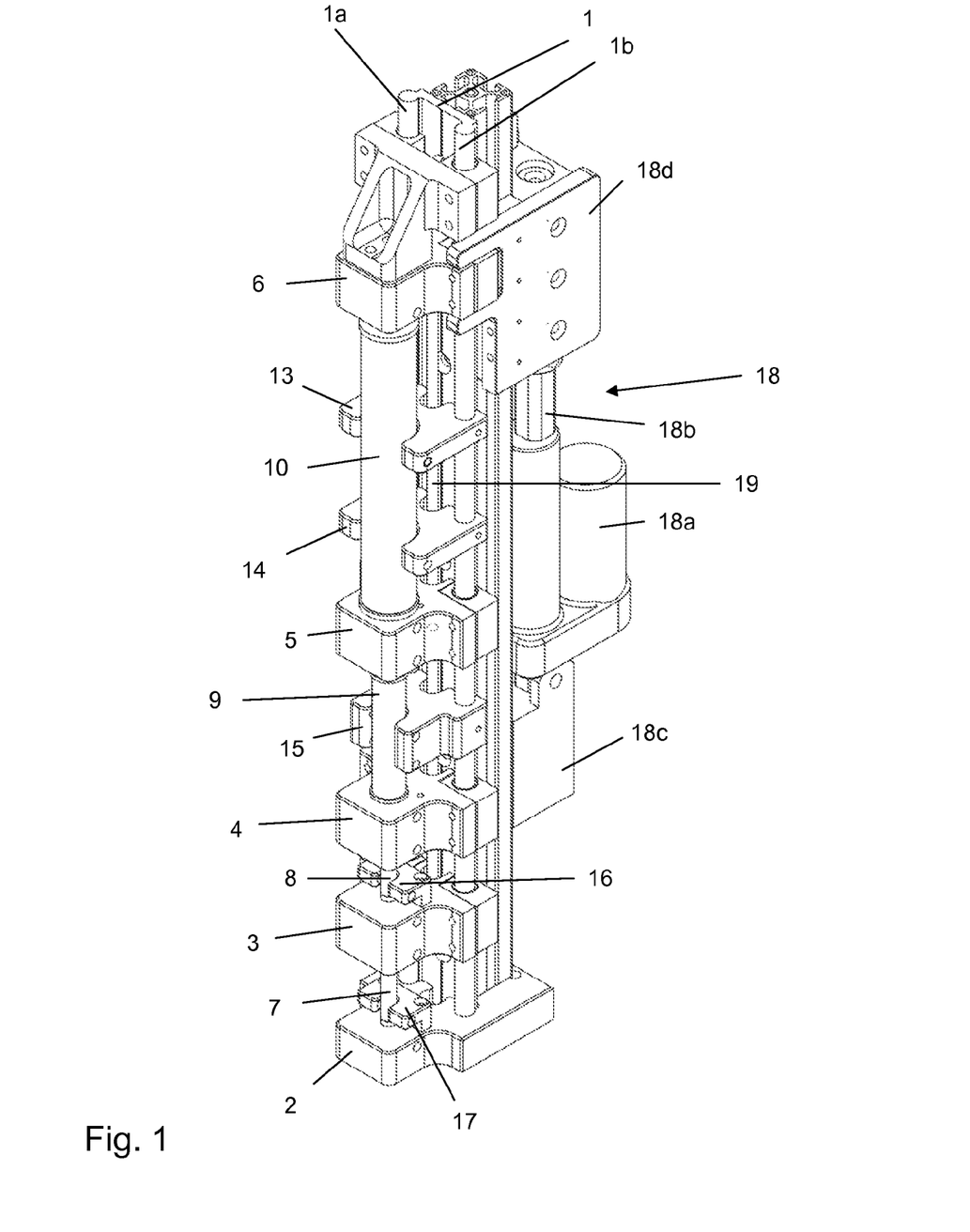
FIG. 1 is a three-dimensional illustration of the clamping device in the clamping position.
Figure 2:
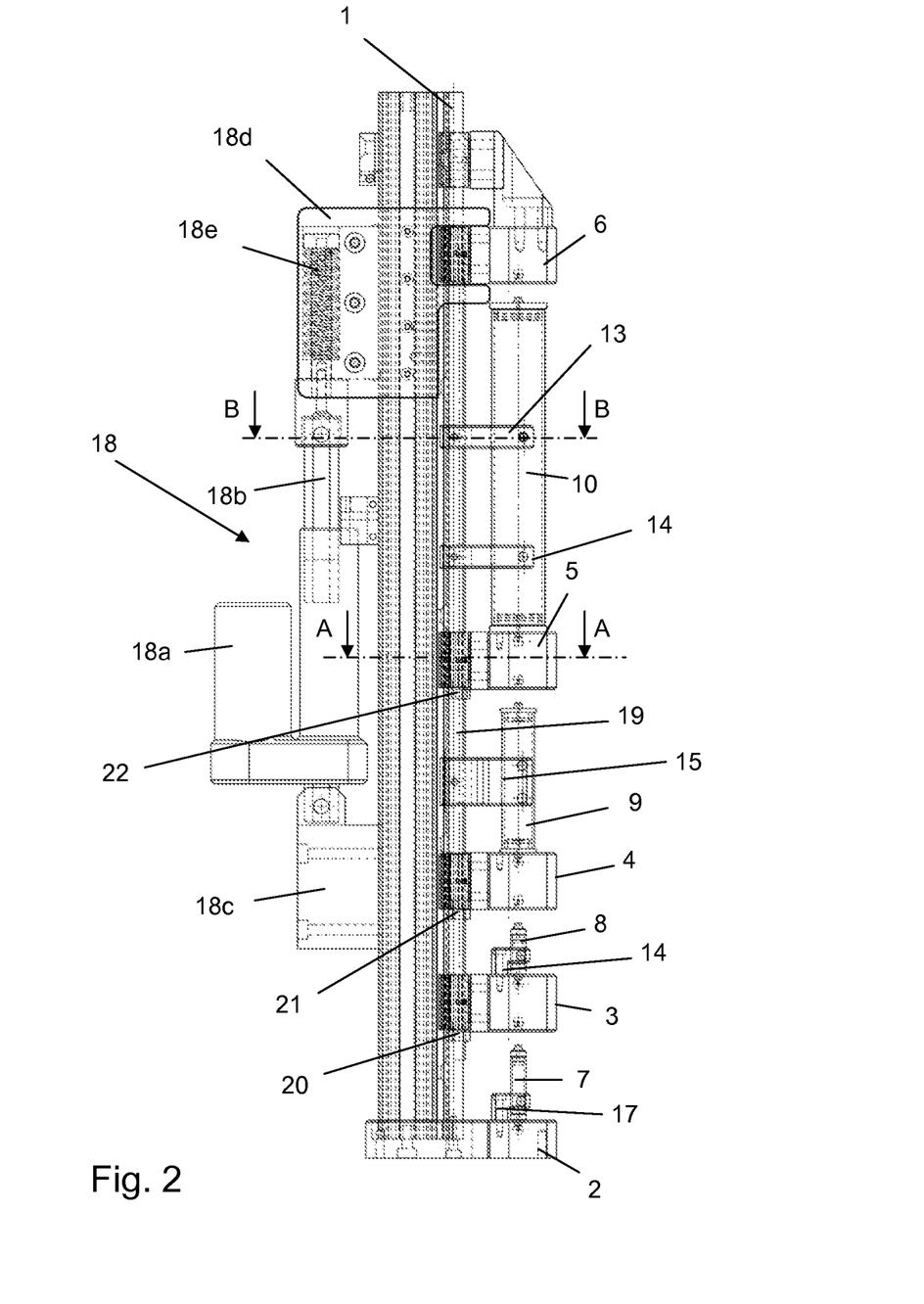
FIG. 2 is a side view of the clamping device in the open position.
Figure 3:
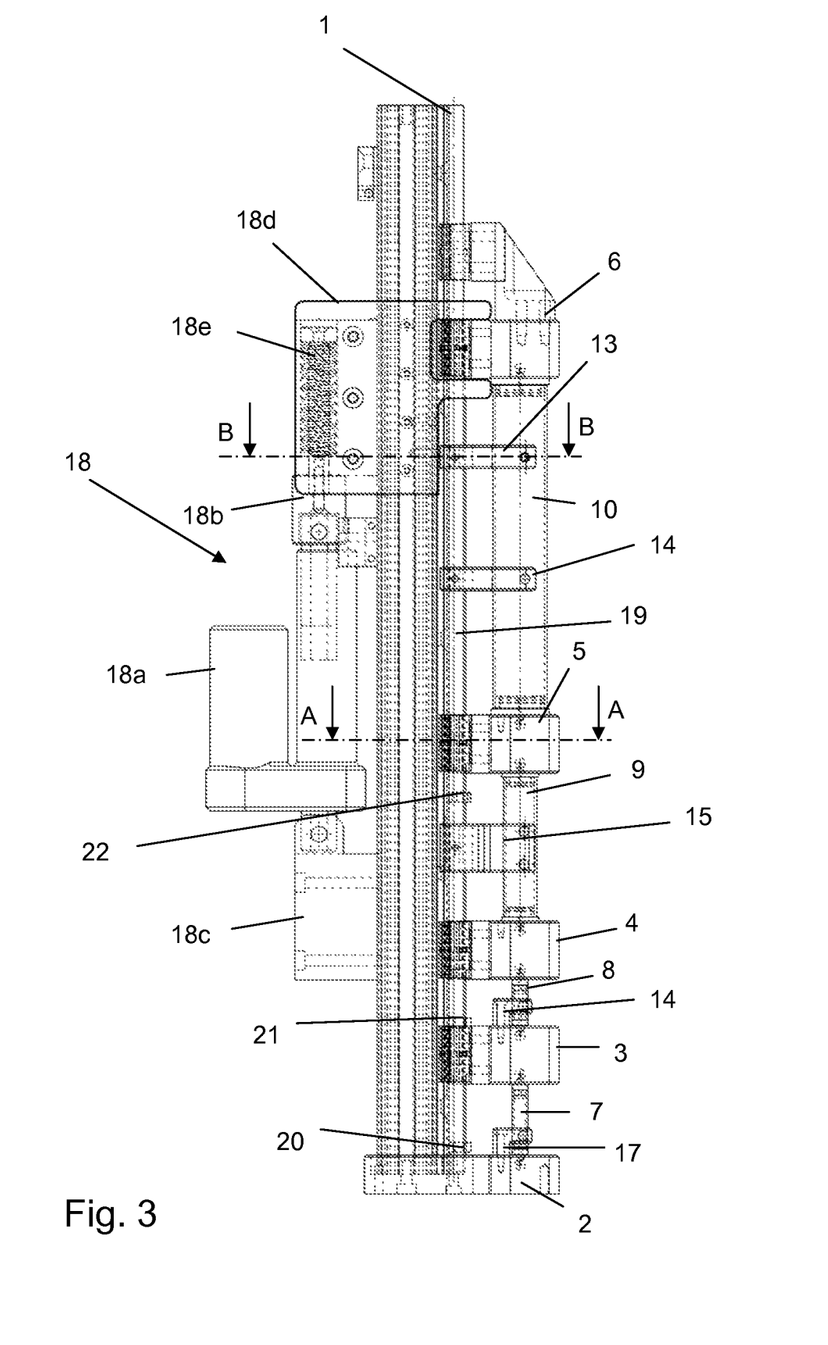
FIG. 3 is a side view of the clamping device in the clamping position.

The clamping device illustrated in FIGS. 1 to 3 has a guiding rail 1, a clamping block 2 which is arranged in a fixed manner on the rail and four clamping blocks 3 to 6 which are retained on the guiding rail so as to be able to be slidingly displaced. In the open position according to FIG. 2, the clamping blocks are spaced so far apart from each other that columns 7 to 10 can each be inserted between two clamping blocks in such a manner that, in the clamping position according to FIG. 3, they are clamped in an axial direction one behind the other between the clamping blocks.

Figure 4:
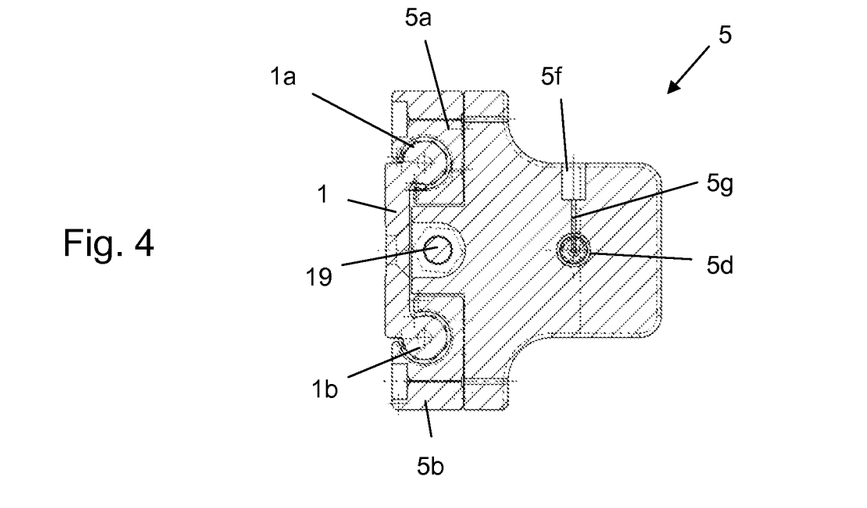
FIG. 4 is a cross-sectional illustration of a clamping block.
Figure 5:
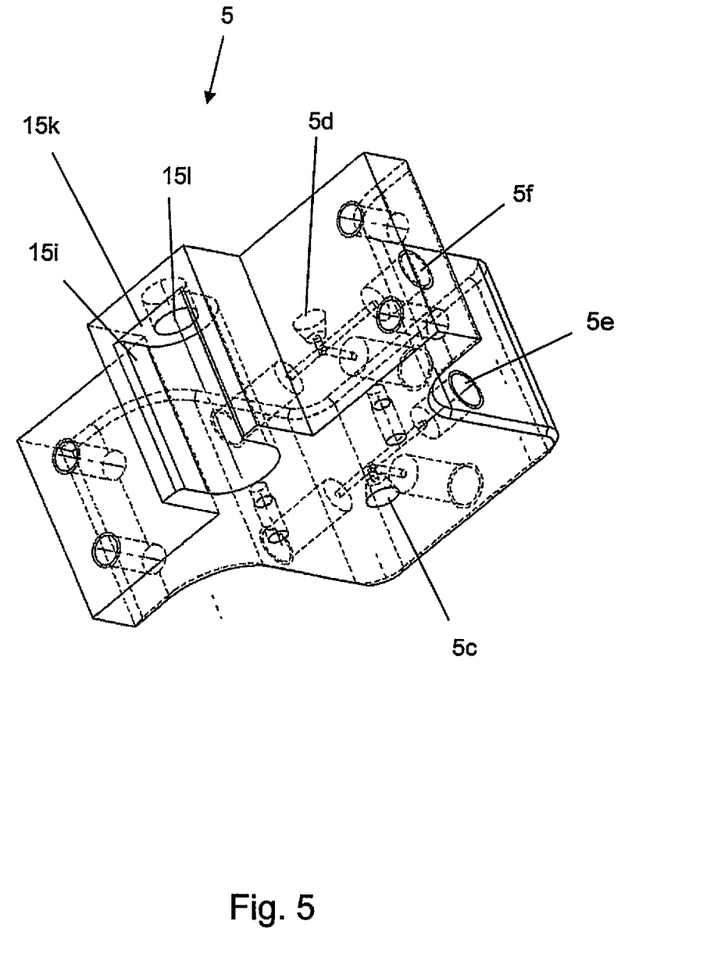
FIG. 5 is a three-dimensional illustration of a clamping block.
Figure 6:
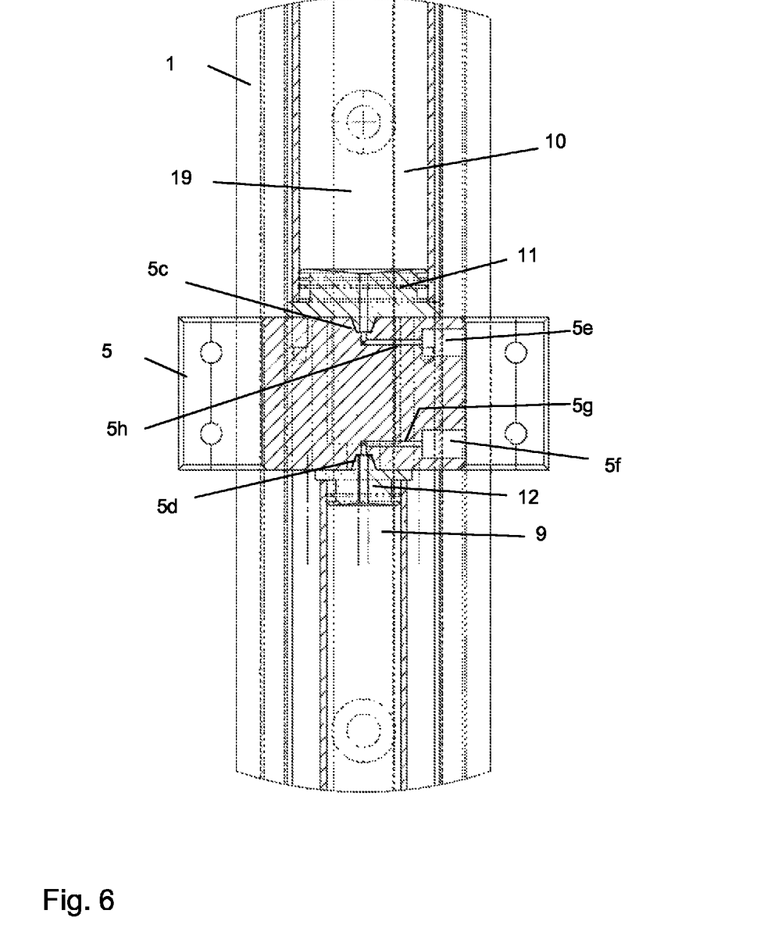
FIG. 6 is a longitudinal section in the region of a clamping block.

With reference to FIGS. 4 to 6, the clamping block 5 will be explained in greater detail below by way of representation of one of the slidingly movable clamping blocks 3 to 6. The guiding rail 1 has two rails 1a, 1b which extend parallel with each other and in the longitudinal direction and which are substantially circular in cross-section and which cooperate with correspondingly complementarily constructed sliding elements 5a, 5b of the clamping block 5. In principle, the sliding elements could be constructed integrally with the remainder of the clamping block. However, since the clamping block advantageously comprises metal, the sliding elements 5a, 5b in the embodiment illustrated are constructed as separate plastics components which are screwed to the remaining clamping blocks. By appropriately selecting the material of the sliding elements 5a, 5b, good sliding properties of the clamping block 5 on the guiding rails 1 can be ensured.

At the sides facing the columns, the clamping blocks 5 are provided with connection pieces 5c, 5d which are constructed in the embodiment illustrated as conical connection pins. The columns 7 to 10 which are intended to be clamped in the clamping device are each provided at the ends thereof with a closure element 11, 12 which is constructed in order to produce the fluid connection between the column and clamping block in a correspondingly complementary manner with respect to the connection piece, that is to say, with a counter-cone. FIG. 6 shows how the connection pieces 5c, 5d of the clamping block 5 cooperate with the closure elements 11, 12 of the columns 10, 9.

Furthermore, at least one fluid channel, but preferably two fluid channels 5g, 5h, which open(s) at one end in the connection piece 5c and 5d and, at the other end, at a connection location 5e, 5f, respectively, is/are provided in the clamping block 5. The connection locations are advantageously provided at one of the two remaining side faces of the clamping block 5.

In FIG. 5, various fluid connections are indicated with dashed lines. Advantageously, however, only those channels which are actually also required for the desired application are formed. However, it would also be entirely conceivable to close any channels which are present and which are not used with a suitable valve or closure plug. It would further be possible to provide the fluid channel for connection of the two connection pieces 5c, 5d. In the case of fluid channels 5g, 5h which extend out laterally, they can be connected to an external valve arrangement in order to provide the flow paths for the desired application.

Figure 7:
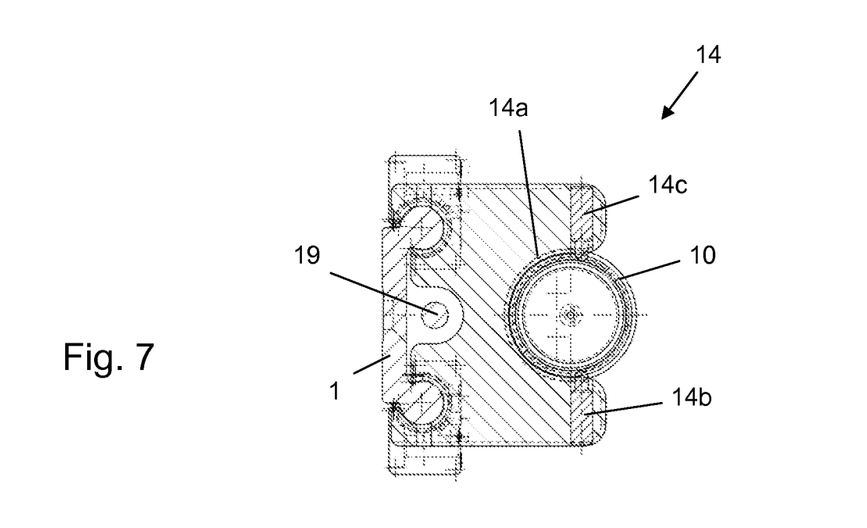
FIG. 7 is a cross-sectional illustration of a column retention member.

According to a preferred embodiment, the guiding rail 1 is orientated vertically so that the columns are also orientated vertically one above the other. In order to clamp the columns, they are inserted only with their closure elements in the associated connection pieces of the respective lower clamping block, a substantially perpendicular orientation of the column automatically being produced. In order to prevent a column which is inserted in the open position of the clamping device from inadvertently being pushed out, additional column retention members 13 to 17 can be provided between the clamping blocks for each column. These column retention members, of which the column retention member 14 is illustrated in greater detail in FIG. 7 by way of example, are also or can also be retained in a fixed manner on the guiding rail in a slidingly displaceable manner. The column retention member has a recess 14a for receiving the corresponding column and is additionally provided with clamping means 14b, 14c which retain the column in the column retention member. Whilst the column retention members 13 to 15 are provided with spacing relative to the clamping blocks, in this embodiment the column retention members 16 and 17 have been secured to the clamping blocks 2 and 3, respectively. This is particularly advantageous with short and thin columns.

The clamping device further has a displacement mechanism 18 which is coupled to the slidingly displaceable clamping block 6 for the displacement thereof along the guiding rail 1. This clamping block forms the end of the row of clamping blocks which are arranged one behind the other and can be displaced by the displacement mechanism in both directions along the guiding rail. The displacement mechanism is in this instance constructed as a linear actuator having a motor 18a and an extension rod 18b. At one end, the displacement mechanism is supported on an abutment 18c and is coupled at the other end thereof via coupling elements 18d to the slidingly displaceable clamping block 6. FIG. 2 shows that the movement of the extension rod 18b is transmitted not directly to the coupling elements 18d, but instead to the coupling elements 18d via a force-limiting compensation spring 18e.

In order to prevent the slidingly displaceable clamping blocks 3 to 6 from all sliding downwards when no columns are inserted, coupling means in the form of a threaded rod 19 have been provided. For each central clamping block 3, 4 and 5, there are fitted to the coupling means 19 carrier elements 20, 21, 22 in the form of nuts which act as a stop for the clamping blocks 3, 4, 5 in the open position of the clamping device according to FIG. 2. FIG. 5 shows that the clamping block at the side thereof facing the guiding rail 1 has a recess 15*i* for receiving the threaded rod. This recess 15*i* is delimited at one side by a wall 15*k* which has a hole 15*l* for the passage of the threaded rod. This wall then comes into contact with the associated carrier element 20, 21, 22 in the open position and prevents the clamping block from sliding down further. The coupling means 19 which is constructed as a threaded rod is securely connected to the slidingly displaceable clamping block 6 which is last in the row so that a displacement of the clamping block 6 by the displacement mechanism 18 at the same time also brings about a corresponding displacement of the coupling means 19 which is constructed as a threaded rod. When the displacement mechanism is moved from the clamping position according to FIG. 3 into the open position according to FIG. 2, when the upper clamping block 6 is displaced, all the central clamping blocks are consequently also displaced upwards via the carrier elements 20, 21, 22 as soon as the carrier elements come into contact with the associated clamping blocks. The clamped columns rest in this instance at the respective lower end thereof on the associated clamping block whilst, in the region of the upper end thereof, an adequate gap is produced with respect to the next clamping block (see FIG. 2). The columns can then be comfortably removed or inserted in this open position. In order to clamp the columns, the displacement mechanism is actuated in the opposing direction so that the uppermost clamping block 6 is moved downwards, that is to say, in the direction of the fixed clamping block 2. In this instance, the coupling means 19 which is constructed as a threaded rod is also displaced downwards so that all the clamping blocks 3, 4, 5 which are located therebetween also move downwards owing to gravitational force until the clamping blocks in the region of their connection pieces come into contact with the associated closure elements of the columns used.

In order to produce a fluid-tight connection of the column and clamping block, there is transmitted by the uppermost clamping block 6 a clamping force which is transmitted via the columns and the clamping blocks as far as the lowest, fixed clamping block. So that this clamping force does not lead to breakage of the columns and in order to compensate for any length tolerances, the force-limiting compensation spring 18*e* is provided. The carrier elements 20, 21, 22 are adjusted in terms of their position on the threaded rod to the corresponding column lengths, the position having such dimensions that, between the carrier element and clamping block in the clamping position according to FIG. 3, a spacing remains so that it is ensured that each column is pressed into the associated clamping blocks thereof with the required clamping force.

From the illustrated embodiment, it can be seen that columns of different sizes can also be used. Should all the column places not be required in an application, a dummy column, for example, a simple high-grade steel pipe which has appropriate connections may simply be used.

The vertical orientation of the clamping device has, on the one hand, the advantage that the central clamping blocks 3, 4 5 slide without mechanical effect from the outer side simply owing to gravitational force from the open position according to FIG. 2 into the closure position according to FIG. 3. The insertion and orientation of the columns in the open position according to FIG. 2 is also facilitated since the columns automatically centre themselves when they are fitted with the closure elements thereof onto the associated lower clamping block. Furthermore, the fluidics (application of the sample, distribution of any air bubbles, flow through the column) remains symmetrical in any case. Furthermore, the clamping device can be flushed in a simple manner. The entire clamping device is in addition constructed so as to be relatively narrow so that a plurality of such clamping devices can be arranged beside each other without an excessively large spatial requirement.

The invention claimed is:

1. Clamping device for clamping at least two columns For sample preparation, the clamping device having at least three clamping blocks retained in a row one behind the other on a guiding rail, wherein first and second clamping blocks of the least three clamping blocks are slidingly displaceable clamping blocks and are connected to a displacement mechanism for displacing the slidingly displaceable clamping blocks between an open position and a clamping position, wherein, in the open position, the at least two columns can be inserted in an axial direction one behind the other between the clamping blocks, and, in the clamping position, the columns are clamped in an axial direction one behind the other between the clamping blocks, in order to produce a fluid connection between the column and at least one of the clamping blocks, wherein the slidingly displaceable clamping blocks interact with the displacement mechanism through coupling means in such a mariner that an actuation of the displacement mechanism from the clamping position into the open position brings about a displacement of all the slidingly displaceable clamping blocks and the columns are released, wherein the coupling means are formed by a rod having carrier elements, wherein the carrier elements come into contact with the clamping blocks only in the direction from the clamping position into the open position, such contact serving to carry the clamping blocks in the direction from the clamping position to into the open position.

2. Clamping device according to claim 1, characterised in that a third clamping block of said at least three clamping blocks is arranged in a fixed manner on the guiding rail.

3. Clamping device according to claim 2, characterised in that the third clamping block of said at least three clamping blocks forms one end of the row of clamping blocks that are arranged one behind the other, and the clamping block at the other end of the row is one of the slidingly displaceable clamping blocks that is operationally connected to the displacement mechanism in order to displace the clamping block at the other end of the row relative to the third clamping block, which is arranged in a fixed manner on the guiding rail.

4. Clamping device according to claim 3, characterised in that a displacement of the slidingly displaceable clamping block connected to the displacement mechanism in the direction of the third clamping block, which is arranged in a fixed manner on the guiding rail, also brings about a displacement of all the clamping blocks arranged therebetween together with the columns as far as the clamping position.

5. Clamping device according to claim 1, characterised in that between at least two clamping blocks at least one column retention member is provided for orientated retention of the columns in the open position.

6. Clamping device according to claim 1, characterised in that the displacement mechanism is constructed to displace the slidingly displaceable clamping block that is connected to the displacement mechanism in both directions along the guiding rail.

7. Clamping device according to claim 1, characterised in that each of the at least three clamping blocks has at least one connection piece, which cooperates with a closure element of the column in the clamping position in order to produce the fluid connection between the column and the clamping block.

8. Clamping device according to claim 7, characterised in that the fluid connection between the connection piece and closure element is produced by means of a cone and counter-cone, the cone being provided either on the connection piece or on the closure element.

9. Clamping device according to claim 7, characterised in that those of the at least three clamping blocks that are arranged between two other clamping blocks of the at least three clamping blocks have two connection pieces which are arranged at opposing sides of thereof.

10. Clamping device according to claim 7, characterised in that each clamping block has at least one fluid channel which opens at one end in the connection piece and at the other end thereof at a connection location.

11. Clamping device according to claim 1, characterised in that the displacement mechanism has at least one force-limiting compensation spring, a displacement force which is produced by means of the displacement mechanism being transmitted via the force-limiting compensation spring to at least one of the slidingly displaceable clamping blocks.

12. Clamping device according to claim 1, characterised in that the slidingly displaceable clamping blocks retained on the guiding rail are connected to the displacement mechanism by way of coupling means in such a mariner that an actuation of the displacement mechanism from the open position into the clamping position and vice versa brings about a displacement of all the slidingly displaceable clamping blocks.

13. Clamping device according to claim 12, characterised in that at least one force-limiting compensation spring is provided between each of the slidingly displaceable clamping blocks and the coupling means in order to limit a clamping force between the column and the clamping blocks.

* * * * *